(12) United States Patent
Hårdemark

(10) Patent No.: US 10,814,143 B2
(45) Date of Patent: Oct. 27, 2020

(54) SYSTEM AND METHOD FOR PROVIDING A RADIATION THERAPY TREATMENT PLAN AND A RADIATION THERAPY MACHINE

(71) Applicant: RaySearch Laboratories AB, Stockholm (SE)

(72) Inventor: Björn Hårdemark, Enskededalen (SE)

(73) Assignee: RaySearch Laboratories AB, Stockholm (SE)

( * ) Notice: Subject to any disclaimer, the term of this patent is extended or adjusted under 35 U.S.C. 154(b) by 331 days.

(21) Appl. No.: 15/563,768

(22) PCT Filed: Mar. 30, 2016

(86) PCT No.: PCT/EP2016/056859
§ 371 (c)(1),
(2) Date: Oct. 2, 2017

(87) PCT Pub. No.: WO2016/156355
PCT Pub. Date: Oct. 6, 2016

(65) Prior Publication Data
US 2018/0078783 A1    Mar. 22, 2018

(30) Foreign Application Priority Data
Apr. 2, 2015 (EP) .................................. 15162331

(51) Int. Cl.
*A61N 5/10* (2006.01)
*G16H 50/50* (2018.01)
(Continued)

(52) U.S. Cl.
CPC ........... *A61N 5/103* (2013.01); *A61N 5/1077* (2013.01); *G06F 19/325* (2013.01); *G16H 50/50* (2018.01);
(Continued)

(58) Field of Classification Search
CPC .................. A61N 5/1031; A61N 5/103; A61N 2005/1032; G06F 19/325; G06F 19/3481; G06F 17/5009
See application file for complete search history.

(56) References Cited

U.S. PATENT DOCUMENTS

2005/0111621 A1\* 5/2005 Riker .................. A61N 5/1031
378/65
2005/0116172 A1   6/2005 Trinkaus et al.
(Continued)

FOREIGN PATENT DOCUMENTS

WO    WO-2011/153639 A2    12/2011

OTHER PUBLICATIONS

Hoffmann et al., "Derivative-free generation and interpolation of convex Pareto optimal IMRT plans," Physics in Medicine and Biology, vol. 51, No. 24, pp. 6349-6369, Dec. 21, 2006.
(Continued)

Primary Examiner — Samuel G Gilbert
(74) Attorney, Agent, or Firm — Faegre Drinker Biddle & Reath LLP

(57) ABSTRACT

A database stores pre-calculated solutions each of which defines a radiation therapy treatment plan for a treatment volume associated with at least one target and at least one organ-at-risk. The pre-calculated solutions are divided into at least two groups each of which includes at least one pre-calculated solution. The pre-calculated solutions in a given group represent radiation therapy treatment plans which share a common beam configuration. A radiation therapy treatment plan ($s_c$) is established based on the pre-calculated solutions as follows. A first user interface receives operator commands specifying criteria for selecting radiation therapy treatment plans from the database, the criteria defining a set of parameters for the treatment volume. In particular, the operator commands jointly specify
(Continued)

criteria for selecting radiation therapy treatment plans from more than one of the at least two groups. When establishing a solution, a preference function is applied on at least two pre-calculated solutions to establish one and only one solution as a radiation therapy treatment plan ($s_c$) meeting the criteria.

20 Claims, 2 Drawing Sheets

(51) Int. Cl.
 G06F 19/00 (2018.01)
 G16H 40/63 (2018.01)
(52) U.S. Cl.
 CPC ...... A61N 2005/1074 (2013.01); G16H 40/63 (2018.01)

(56) References Cited

U.S. PATENT DOCUMENTS

2007/0081629 A1* 4/2007 Yin ............... A61N 5/1031 378/65
2013/0197878 A1* 8/2013 Fiege ............ A61N 5/1031 703/2

OTHER PUBLICATIONS

Rasmus Bokrantz, "Multicriteria optimization for volumetric-modulated arc therapy by decomposition into a fluence-based relaxation and a segment weight-based restriction," Medical Physics, vol. 39, No. 11, pp. 6712-6725, Nov. 1, 2012.

Rasmus Bokrantz, "Multicriteria optimization for managing tradeoffs in radiation therapy treatment planning," KTH Royal Institute of Technology, Stockholm, Sweden, Jun. 14, 2013.

* cited by examiner

SYSTEM AND METHOD FOR PROVIDING A RADIATION THERAPY TREATMENT PLAN AND A RADIATION THERAPY MACHINE

This application is the National Stage of International Application No. PCT/EP2016/056859, filed Mar. 30, 2016, and claims benefit of European Patent Application No. 15162331.1 filed Apr. 2, 2015.

THE BACKGROUND OF THE INVENTION AND PRIOR ART

The present invention relates generally to radiation therapy and strategies for selecting a suitable radiation therapy treatment plan for a given treatment volume. More particularly the invention relates to a system according to the preamble of claim 1, a method according to the preamble of claim 8 and a radiation therapy machine according to the preamble of claim 15. The invention also relates to a computer program product, a computer readable medium and a radiation therapy method.

Treatment planning for radiation therapy inherently involves tradeoffs, for instance between tumor control and normal tissue sparing, between time-efficiency and dose quality, and between nominal plan quality and robustness. Methods are therefore desirable that can facilitate the decision making related to such tradeoffs.

In so-called multi-criteria optimization methods a representative set of treatment plans is first calculated. The most appropriate plan contained in this representation is then selected by the treatment planner through continuous interpolation between the pre-calculated alternatives. These alternatives constitute a subset of the set of Pareto optimal plans, which are plans with such characteristics that no criterion can be improved without a sacrifice in another.

WO 2011/153639 shows a fluence and beam orientation optimization package for radiotherapy optimization, called PARETO (Pareto-Aware Radiotherapy Evolutionary Treatment Optimization) that makes use of a multi-objective genetic algorithm capable of optimizing several objective functions simultaneously and mapping the structure of their trade-off surface efficiently and in detail. PARETO generates a database of Pareto non-dominated solutions and allows the graphical exploration of tradeoffs between multiple planning objectives during intensity-modulated radiation therapy (IMRT) treatment planning. PARETO offers automated and truly multi-objective treatment plan optimization, which does not require any objective weights to be chosen, and therefore finds a large sample of optimized solutions defining a trade-off surface, which represents the range of compromises that are possible.

US 2005/0116172 describes a planning tool for the interactive selection of control variables of a radiation therapy plan from a database comprising a plurality of pre-calculated solutions. Here, each solution represents a radiation therapy plan which, from a technical point of view, consists of a plurality of control variables or instructions. Each solution also has characteristic values for radiation doses for a target volume and at least one risk volume, which are stored in the database. A plurality of axes are visibly represented on a display device as radiation dose scales for the target volume and the at least one risk volume, for the formation of at least one risk axis and one target axis. The characteristic values of the radiation doses for at least a plurality of the stored solutions are allocated to the respective corresponding axes in such a way that an acceptance interval is created for each risk axis and the target axis, said acceptance interval determining a common planning area for all axes. Said planning area is visibly emphasized on the display device in relation to the surrounding field.

Problems Associated with the Prior Art

Consequently, various solutions are known for interactive planning of a radiation therapy treatment. However, there is yet no solution capable of prioritizing between solutions that involve different beam configurations, i.e. where the number of radiation beams vary, the angles between the radiation sources vary, and/or the radiation modality is dissimilar (e.g. the radiation source emitting photons, electrons, protons, carbon or helium ions).

SUMMARY OF THE INVENTION

The object of the present invention is therefore to solve the above problem, and thus offer efficient strategies for establishing a suitable radiation therapy treatment plan based on a set of pre-calculated solutions ranging over a very broad spectrum of therapy characteristics.

According to one aspect of the invention, the object is achieved by the initially described system, wherein the pre-calculated solutions are divided into at least two groups each of which comprises at least one pre-calculated solution. The pre-calculated solutions in a given group represent radiation therapy treatment plans which share a common beam configuration. A first user interface is configured to receive operator commands, which jointly specify criteria for selecting radiation therapy treatment plans from more than one of the at least two groups. The data processor is configured to apply a preference function on at least one pre-calculated solution in the at least two groups to establish one and only one solution as the radiation therapy treatment plan meeting the criteria.

This system is advantageous because it provides a common user interface for filtering among the pre-calculated solutions in a well-organized and intuitive manner also if the solutions involve different beam configurations and/or employ dissimilar radiation modality. Naturally, the treatment-planning process can thereby be made very time-efficient.

According to one preferred embodiment of this aspect of the invention, the preference function is arranged to establish the pre-calculated solution in the group of the at least two groups which pre-calculated solution has a largest margin to the criteria. Thus, not only an acceptable solution is found, however the system distinguishes the best solution relative to the criteria in question.

Preferably, the data processor is configured to calculate the preference function based on the criteria specified by the operator commands. Hence, it is guaranteed that the preference function is calibrated adequately.

According to another preferred embodiment of this aspect of the invention, the common beam configuration shared by the radiation therapy treatment plans in a group of the at least two groups is specifically defined in terms of: a number of radiation beams used being equal, a set of mutual angles between the radiation sources used being equal, and a type of particles emitted from the radiation sources being equal. Thereby, it is rendered relatively straightforward to filter out a solution within each group of radiation therapy treatment plans.

According to yet another preferred embodiment of this aspect of the invention, if no pre-calculated solution in a group of the at least two groups meets the criteria, the data processor is further configured to interpolate between at least two pre-calculated solutions in the group to determine a composite radiation therapy treatment plan meeting the criteria. The second user interface is then configured to present the composite radiation therapy treatment plan as the radiation therapy treatment plan established by the data processor to meet the criteria. Consequently, also a group that does not prima facie contain a solution that matches the criteria may provide a radiation therapy treatment plan.

According to still another preferred embodiment of this aspect of the invention, the second user interface is configured to present an option for selecting a potential interpolation between two or more pre-calculated solutions in a group of the at least two groups of pre-calculated solutions. If an operator command is received via the first user interface, which operator command designates selection of a potential interpolation between two or more pre-calculated solutions in a selected group of the at least two groups of pre-calculated solutions, the data processor is configured to interpolate between at least two pre-calculated solutions in the selected group to determine a composite radiation therapy treatment plan meeting the criteria. It is presumed that at least one of the at least two pre-calculated solution plans meet the criteria. Further, the composite radiation therapy treatment plan meets the criteria with a better margin than any single radiation therapy treatment plan in the selected group. Then, the second user interface is configured to present the composite radiation therapy treatment plan as the radiation therapy treatment plan established by the data processor to meet the criteria. Thereby, even if a group does contain at least one solution that matches the criteria, the user may cause the system to provide a better interpolated solution.

Preferably, in either of the above two cases, the data processor is configured to interpolate linearly between the at least two pre-calculated solutions to determine the composite radiation therapy treatment plan.

According to another aspect of the invention, the object is achieved by the method described initially, wherein the pre-calculated solutions are divided into at least two groups each of which contains at least one pre-calculated solution. The pre-calculated solutions in a given group represent radiation therapy treatment plans, which share a common beam configuration. The method further involves receiving, via the first user interface, operator commands which jointly specify criteria for selecting radiation therapy treatment plans from more than one of the at least two groups. The method also involves applying a preference function on at least one pre-calculated solution in the at least two groups to establish one and only one solution as the radiation therapy treatment plan meeting the criteria. The advantages of this method, as well as the preferred embodiments thereof, are apparent from the discussion above with reference to the proposed system.

According to a further aspect of the invention, the object is achieved by a computer program product, which is loadable into the memory of a computer, and includes software for performing the steps of the above proposed method when executed on a computer.

According to another aspect of the invention, the object is achieved by a computer readable medium, having a program recorded thereon, where the program is to make a computer perform the method proposed above when the program is loaded into the computer.

According to yet another aspect of the invention, the object is achieved by a radiation therapy machine configured to receive a radiation therapy treatment plan established by the above-proposed method, and carry out therapy in accordance with the received radiation therapy treatment plan.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings.

DESCRIPTION OF PREFERRED EMBODIMENTS OF THE INVENTION

Figure 1:
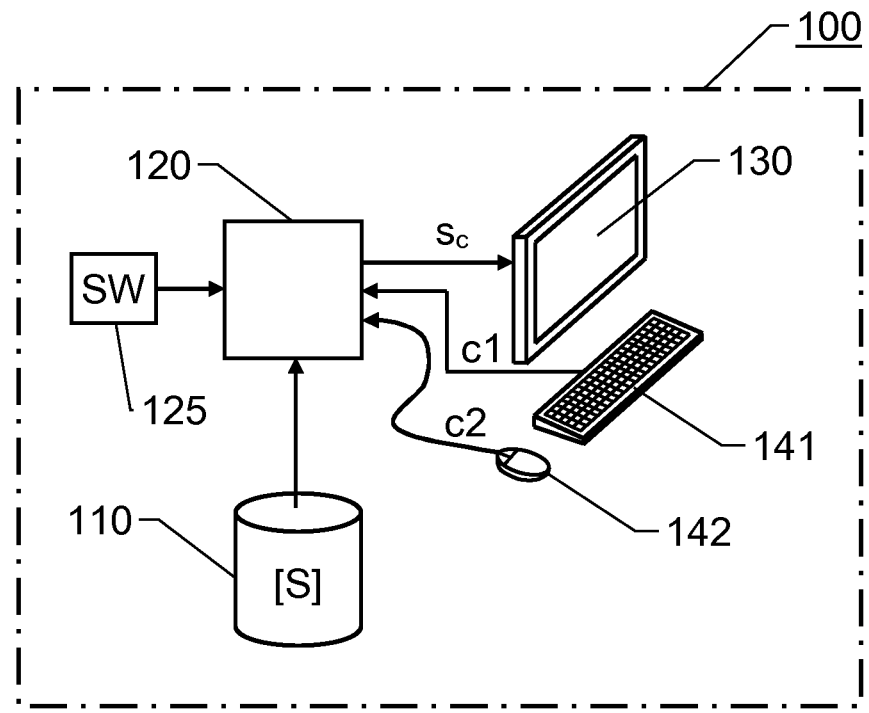
FIG. 1 shows a block diagram over a system according to one embodiment of the invention.

Initially, we refer to FIG. 1, which shows a block diagram over a system 100 according to one embodiment of the invention for providing a radiation therapy treatment plan $s_c$. The system includes a database 110, a data processor 120, and first and second user interfaces 141/142 and 130 for receiving operator commands and providing the radiation treatment plan $s_c$ respectively.

Figure 2:
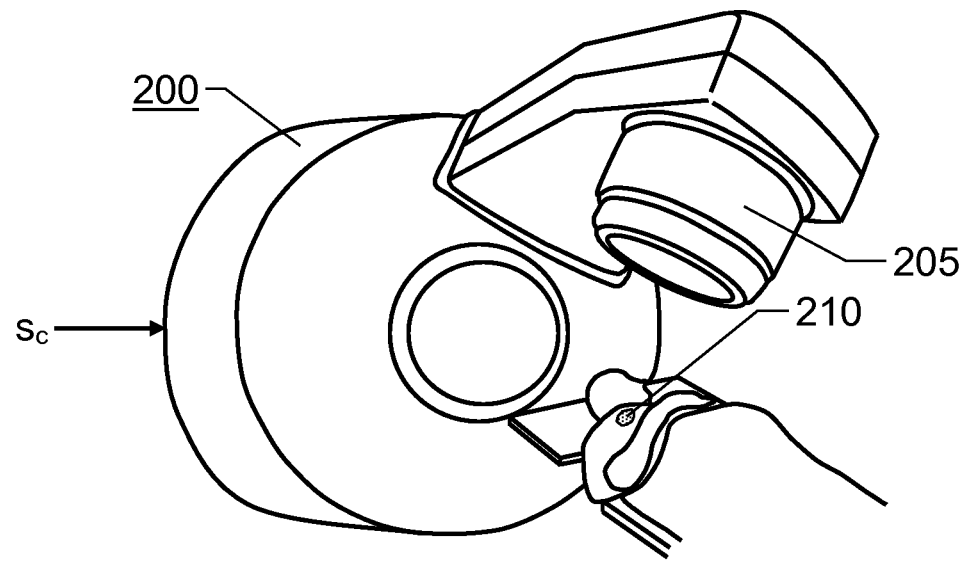
FIG. 2 schematically illustrates a radiation therapy machine according to the invention.

The database 110 stores pre-calculated solutions [S] each of which defines a radiation therapy treatment plan for a particular treatment volume 210 (see FIG. 2). The treatment volume 210, in turn, is associated with at least one target and at least one organ-at-risk, typically corresponding to a tumor to be treated and healthy tissues in which the radiation dose should be kept below certain levels respectively. The pre-calculated solutions [S] in the database 110 are divided into at least two groups, which each includes at least one pre-calculated solution. Here, the pre-calculated solutions in a given group represent radiation therapy treatment plans which share a common beam configuration. This preferably means that the pre-calculated solutions in a particular group all represent radiation therapy treatment plans with the same number of radiation beams, where a set of mutual angles between the radiation sources used are equal, and where the type of particles emitted from the radiation sources are the same. In other words, if one or more of: the number of radiation beams, the angles between the radiation sources and the particles emitted differ between two radiation therapy treatment plans, the plans are organized in different groups in the database 110.

The first user interface is configured to receive operator commands c1 and c2 that specify criteria for selecting radiation therapy treatment plans from the database 110. Consequently, the first user interface contains at least one input means, which in FIG. 1, are exemplified by a keyboard 141 (for entering text, numbers and commands) and a mouse 142 (for selecting and confirming selections). However, of course, according to the invention, any other form of input means are equally well conceivable, e.g. a touchpad, a touch screen, a voice controlled interface and/or a gaze controlled interface. In any case, the criteria specified by the operator commands c1 and c2 define a set of parameters for the treatment volume 210. Moreover, the first user interfaces 141 and 142 are configured to receive operator commands c1 and c2, which jointly specify criteria for selecting radiation therapy treatment plans from more than one of the above-mentioned groups.

Based on the pre-calculated solutions [S] in the database 110, the data processor 120 is configured to establish any solutions [S] which meet the criteria. The second user interface 130 is configured to present at least one radiation therapy treatment plan established by the data processor 120 as a radiation therapy treatment plan $s_c$ meeting the criteria. Thus, the second user interface 130 typically contains an output means in the form of a computer display. However, alternatively or additionally, the second user interface 130 may include an acoustic channel and/or any other type of data output port.

When establishing any solutions that meet the criteria specified by the operator commands c1 and c2, the data processor 120 is configured to apply a preference function on at least one pre-calculated solution in at least two groups of the database 110. For example, if more than one pre-calculated solution in a group are found to meet the criteria, the data processor 120 is configured to apply such a preference function to these pre-calculated solutions. The preference function establishes one and only one pre-calculated solution in the group as the radiation therapy treatment plan $s_c$ meeting the criteria. Thereby, a treatment planner can filter out pre-calculated solutions [S] representing radiation therapy treatment plans over a very broad spectrum in a highly time-efficient and convenient manner.

According to one embodiment of the invention, the preference function is specifically arranged to establish the pre-calculated solution $s_c$ in the group which has a largest margin to the criteria, since, generally, a larger margin is more preferable than a smaller margin.

Further, the preference function is adaptable, and the data processor 120 is configured to calculate the preference function based on the criteria specified by the operator commands c1 and c2.

Depending on the properties of the treatment volume and the operator commands c1 and c2 received, it may, of course, be the case that no pre-calculated solution in a group meets the criteria. In such a case, the data processor 120 is preferably configured to interpolate (e.g. linearly) between at least two pre-calculated solutions in the group aiming to determine a composite radiation therapy treatment plan which actually meets the criteria. Here, the second user interface 130 is configured to present the composite radiation therapy treatment plan as the radiation therapy treatment plan $s_c$ established by the data processor to meet the criteria. Hence, a treatment planner need not be informed that there was no matching pre-calculated solution in the database 110, and still he/she is provided with a radiation therapy treatment plan meeting the criteria.

Naturally, depending on the criteria, it may be impossible to establish a radiation therapy treatment plan that meets the criteria based on the pre-calculated solutions in the database 110. In such a case, the second user interface 13 is preferably configured to present a message indicating that no solution could be established as a radiation therapy treatment plan meeting the criteria of the operator commands c1 and c2.

Conversely, even though there is one or more pre-calculated solutions in a group that meet the criteria, a still better solution may be attainable. Therefore, according to one embodiment of the invention, the second user interface 130 is further configured to present an option for selecting a potential interpolation between two or more pre-calculated solutions in a group of solutions [S] in the database 110. Thereby, the treatment planner may enter an operator command c1 and/or c2, via the first user interface 141 and/or 142, which designates selection of a potential interpolation between two or more pre-calculated solutions in a selected group. In response to receiving such a command, the data processor 120 is configured to interpolate (e.g. linearly) between at least two pre-calculated solutions in the selected group to determine a composite radiation therapy treatment plan meeting the criteria. It should be noted that less than all of the at least two pre-calculated solutions that form the basis for the composite radiation therapy treatment plan, as such, need to meet the criteria. In fact, none of the underlying solutions themselves needs to meet the criteria. In any case, the composite radiation therapy treatment plan meets the criteria with better margin than any single radiation therapy treatment plan in the selected group.

Also here, the second user interface 130 is configured to present the composite radiation therapy treatment plan as the radiation therapy treatment plan $s_c$ established by the data processor to meet the criteria.

FIG. 2 schematically illustrates a radiation therapy machine 200 according to the invention. The radiation therapy machine 200 is configured to receive the above-mentioned radiation therapy treatment plan $s_c$ established via the system 100. The radiation therapy machine 200 is further configured to carry out therapy in respect of the treatment volume 210 by controlling at least one radiation source 205 of the machine in accordance with the received radiation therapy treatment plan $s_c$. Thus, the at least one radiation source 205 may be configured to emit radiation towards the treatment volume 210, for instance in the form of photons, electrons, protons, carbon or helium ions.

The data processor 120 preferably contains, or is in communicative connection with a memory unit 125 storing a computer program product SW, which contains software for making the data processor 120 execute the above-described actions when the computer program product SW is run on the data processor 120.

Figure 3:
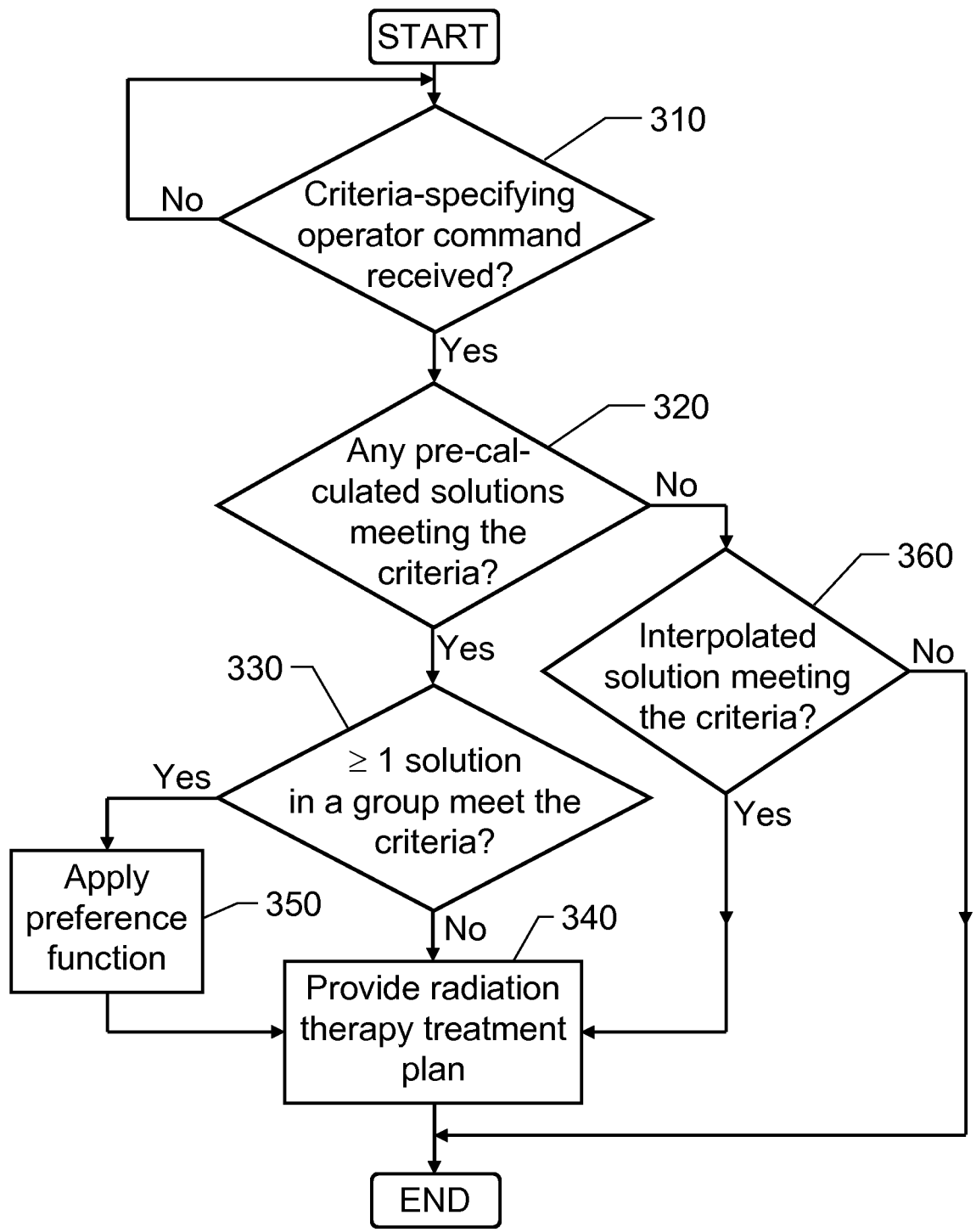
FIG. 3 illustrates, by means of a flow diagram, the general method according to the invention for providing a radiation therapy treatment plan.

In order to sum up, and with reference to the flow diagram in FIG. 3, we will now describe the general method executed in the data processor 120 according to the invention when providing a radiation therapy treatment plan.

A first step 310 checks if operator commands have been received which specify criteria for establishing radiation therapy treatment plans based on a database of pre-calculated solutions defining a respective radiation therapy treatment plan for a treatment volume, which, in turn, is associated with at least one target and at least one organ-at-risk. The pre-calculated solutions are divided into at least two groups each of which contains at least one pre-calculated solution. The pre-calculated solutions in a given group represent radiation therapy treatment plans which share a common beam configuration.

If such operator commands are received in step 310, a step 320 follows; and otherwise, the procedure loops back and stays in step 310.

In step 320, it is checked if any pre-calculated solutions in the database can be found which meet the criteria; and if so, a step 330 follows. Otherwise, the procedure continues to a step 360.

Step 330 checks if, in step 320, more than one pre-calculated solution in a group was found to be a radiation therapy treatment plan meeting the criteria, and If so, a step 350 follows. Otherwise the procedure continues to a step 340 in which the pre-calculated solution is provided as a radiation therapy treatment plan established to meet the criteria specified via the operator commands.

In step 350, a preference function is applied to the pre-calculated solutions in the group meeting the criteria in order to establish one and only one solution in the form of radiation therapy treatment plan that meets the criteria. As mentioned above, the preference function may be applied to radiation therapy treatment plans which themselves all meet the criteria (to establish a composite plan, e.g. based on interpolation, that meet the criteria with an even better margin); or, the preference function may be applied to a number of radiation therapy treatment plans of which one or more does not meet the criteria (to establish a composite plan, e.g. based on interpolation, that does meet the criteria), see step 360 below.

After step 350, the procedure continues to step 340 for providing the established radiation therapy treatment plan, and subsequently, the procedure ends.

Step 360 checks if it is possible to establish any interpolated solutions that meet the criteria, and if so, analogous to step 350, the plan meeting the criteria with a largest margin is selected as the established plan that meet the criteria. Then, step 340 follows.

If, however, in step 360 no interpolated solution can be established that meets the criteria, the procedure ends. Preferably, in connection with this, a user interface presents a message indicating that no solution could be established as a radiation therapy treatment plan meeting the criteria specified by the operator commands.

All of the process steps, as well as any sub-sequence of steps, described with reference to FIG. 3 above may be controlled by means of a programmed computer apparatus. Moreover, although the embodiments of the invention described above with reference to the drawings comprise a computer apparatus and processes performed in a computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A system for providing a radiation therapy treatment plan ($s_c$), the system comprising:
a database storing pre-calculated solutions each of which defines a radiation therapy treatment plan for a treatment volume associated with at least one target and at least one organ-at-risk, wherein the pre-calculated solutions are divided into at least two groups each of which comprises at least one pre-calculated solution, and the pre-calculated solutions in a given group represent radiation therapy treatment plans which share a common beam configuration;
a first user interface configured to receive operator commands specifying criteria for selecting radiation therapy treatment plans from more than one of the at least two groups in the database, the criteria defining a set of parameters for the treatment volume;
a data processor configured to establish any solutions which meet the criteria; and
a second user interface configured to present radiation therapy treatment plans that are established by the data processor as radiation therapy treatment plans ($s_c$) meeting the criteria;
wherein, for each of the at least two groups having pre-calculated solutions meeting the criteria, the data processor is configured to apply a preference function on the pre-calculated solutions meeting the criteria to establish one solution per group to be presented via the second user interface.

2. The system according to claim 1, wherein the preference function is arranged to establish the radiation therapy treatment plan ($s_c$) meeting the criteria as a pre-calculated solution ($s_c$) in one of the at least two groups which pre-calculated solution ($s_c$) has a largest margin to the criteria.

3. The system according to claim 1, wherein the data processor is configured to calculate the preference function based on the criteria specified by the operator commands.

4. The system according to claim 1, wherein the common beam configuration shared by the radiation therapy treatment plans in a group of the at least two groups is defined in terms of:
a number of radiation beams used being equal,
a set of mutual angles between radiation sources used being equal, and
a type of particles emitted from the radiation sources being equal.

5. The system according to claim 1, wherein, if no pre-calculated solution in a group of the at least two groups meets the criteria:
the data processor is further configured to interpolate between at least two pre-calculated solutions to determine a composite radiation therapy treatment plan meeting the criteria, and
the second user interface is configured to present the composite radiation therapy treatment plan as the radiation therapy treatment plan ($s_c$) established by the data processor to meet the criteria.

6. The system according to claim 5, wherein the data processor is configured to interpolate linearly between the at least two pre-calculated solutions to determine the composite radiation therapy treatment plan.

7. The system according to claim 1, wherein:
the second user interface is configured to present an option for selecting a potential interpolation between two or more pre-calculated solutions in a group of the at least two groups of pre-calculated solutions, and in response to receiving, via the first user interface, an operator command designating selection of a potential interpolation between two or more pre-calculated solutions in a selected group of the at least two groups of pre-calculated solutions,
the data processor is configured to interpolate between at least two pre-calculated solutions in the selected group to determine a composite radiation therapy treatment plan meeting the criteria, wherein at least one of the at least two pre-calculated solution plans meet the criteria, and the composite radiation therapy treatment plan meeting the criteria with a better margin than any single radiation therapy treatment plan in the selected group, and
the second user interface is configured to present the composite radiation therapy treatment plan as the radiation therapy treatment plan ($s_c$) established by the data processor to meet the criteria.

8. The system according to claim 7, wherein the data processor is configured to interpolate linearly between the at least two pre-calculated solutions to determine the composite radiation therapy treatment plan.

9. A method of providing a radiation therapy treatment plan ($s_c$) based on a database storing pre-calculated solutions each of which defines a radiation therapy treatment plan for a treatment volume associated with at least one target and at least one organ-at-risk, the method comprising:
receiving, via a first user interface, operator commands specifying criteria for selecting radiation therapy treatment plans from the database, the criteria defining a set of parameters for the treatment volume;
establishing any solutions which meet the criteria;
presenting, via a second user interface, at least one radiation therapy treatment plan ($s_c$) that is established to be a radiation therapy treatment plan meeting the criteria, wherein the pre-calculated solutions are divided into at least two groups each of which comprises at least one pre-calculated solution, and the pre-calculated solutions in a given group representing radiation therapy treatment plans which share a common beam configuration; and
for each of the at least two groups having pre-calculated solutions meeting the criteria, applying a preference function on the pre-calculated solutions meeting the criteria to establish one solution per group to be presented via the second user interface.

10. The method according to claim 9, wherein the preference function is arranged to establish the radiation therapy treatment plan ($s_c$) meeting the criteria as a pre-calculated solution in one of the at least two groups which pre-calculated solution has a largest margin to the criteria.

11. The method according to claim 9, comprising:
calculating the preference function based on the criteria specified by the operator commands.

12. The method according to claim 9, wherein the common beam configuration shared by the radiation therapy treatment plans in a group of the at least two groups is defined in terms of:
a number of radiation beams used being equal,
a set of mutual angles between radiation sources used being equal, and
a type of particles emitted from the radiation sources being equal.

13. The method according to claim 9, wherein, if no pre-calculated solution in a group of the at least two groups meets the criteria, the method comprises:
interpolating between at least two pre-calculated solutions to determine a composite radiation treatment plan meeting the criteria, and
presenting, via the second user interface, the composite radiation therapy treatment plan as the radiation therapy treatment plan ($s_c$) meeting the criteria.

14. The method according to claim 13, comprising:
interpolating linearly between the at least two pre-calculated solutions to determine the composite radiation therapy treatment plan.

15. The method according to claim 9, comprising:
presenting, via the second user interface, an option for selecting a potential interpolation between two or more pre-calculated solutions in a selected group of the at least two groups of pre-calculated solutions; if an operator command is received via the first user interface, said operator command selecting the potential interpolation between the two or more pre-calculated solutions in the selected group of the at least two groups of pre-calculated solutions;
interpolating between at least two pre-calculated solutions in the selected group to determine a composite radiation therapy treatment plan meeting the criteria, wherein at least one of the at least two pre-calculated solution plans meet the criteria, and the composite radiation therapy treatment plan meeting the criteria with a better margin than any single radiation therapy treatment plan in the selected group; and
presenting, via the second user interface, the composite radiation therapy treatment plan as the radiation therapy treatment plan ($s_c$) established by the data processor which meets the criteria.

16. The method according to claim 15, comprising:
interpolating linearly between the at least two pre-calculated solutions to determine the composite radiation therapy treatment plan.

17. A radiation therapy machine, comprising:
a radiation source configured to emit radiation towards a treatment volume,
wherein the radiation therapy machine is configured to receive a radiation therapy treatment plan ($s_c$) provided by the method according to claim 9, and
carry out therapy in respect of the treatment volume by controlling the radiation source in accordance with the received radiation therapy treatment plan ($s_c$).

18. A computer program product loadable into a memory of at least one computer, comprising software for performing the steps of the method according to claim 9 when executed on the at least one computer.

19. A non-transitory computer readable medium having a program recorded thereon, where the program is to make at least one computer perform the steps of claim 9.

20. A radiation therapy method comprising:
receiving a radiation therapy treatment plan ($s_c$) provided by the method according to claim 9, and
carrying out therapy in respect of a treatment volume by controlling a radiation source in accordance with the received radiation therapy treatment plan ($s_c$).

* * * * *